United States Patent
Okojie (10) Patent No.: US 9,766,053 B1
(45) Date of Patent: Sep. 19, 2017

(54) MATERIAL DAMAGE SYSTEM AND METHOD FOR DETERMINING SAME

(75) Inventor: Robert Okojie, Strongsville, OH (US)

(73) Assignee: The United States of America as Represented by the Administrator of NASA, Washington, DC (US)

( * ) Notice: Subject to any disclaimer, the term of this patent is extended or adjusted under 35 U.S.C. 154(b) by 1472 days.

(21) Appl. No.: 13/301,249

(22) Filed: Nov. 21, 2011

(51) Int. Cl.
| | |
|---|---|
| *G01B 7/02* | (2006.01) |
| *G01B 7/04* | (2006.01) |
| *G01N 17/04* | (2006.01) |
| G01N 3/56 | (2006.01) |
| G01N 27/20 | (2006.01) |
| G01N 27/24 | (2006.01) |

(52) U.S. Cl.
CPC ............... *G01B 7/02* (2013.01); *G01B 7/044* (2013.01); *G01N 17/04* (2013.01); *G01N 3/56* (2013.01); *G01N 27/20* (2013.01); *G01N 27/24* (2013.01)

(58) Field of Classification Search
CPC .......... G01B 7/02; G01B 7/044; G01N 27/20; G01N 17/04; G01N 27/24; G01N 3/56; G01N 17/00; H01C 3/08
See application file for complete search history.

(56) References Cited

U.S. PATENT DOCUMENTS

| | | | |
|---|---|---|---|
| 3,018,663 A | 1/1962 | Dunlop | |
| 3,078,707 A | 2/1963 | Weaver | |
| 3,307,401 A | 3/1967 | Bachman | |
| 3,340,727 A | 9/1967 | Bracalente et al. | |
| 3,357,237 A | 12/1967 | Le Bel | |
| 3,512,413 A | 5/1970 | Blaus Janis et al. | |
| 4,338,563 A | 7/1982 | Rhoades et al. | |
| 4,372,693 A * | 2/1983 | Lutz | G08B 17/06 324/519 |
| 4,655,077 A | 4/1987 | Purvis et al. | |
| 5,243,297 A | 9/1993 | Perkins et al. | |
| 6,383,451 B1 | 5/2002 | Kim et al. | |
| 6,590,403 B1 * | 7/2003 | Gramer | F02K 9/26 324/700 |
| 7,313,947 B2 | 1/2008 | Harris et al. | |
| 2004/0223636 A1 * | 11/2004 | Edic | G06T 7/0012 382/131 |
| 2007/0120572 A1 | 5/2007 | Chen et al. | |
| 2009/0243585 A1 | 10/2009 | Andarawis et al. | |

OTHER PUBLICATIONS

Yildiz, Potential Ambient Energy-Harvesting Sources and Techniques, Oct. 2009, The Journal of Technology Studies, pp. 1, 4 and 5.*

* cited by examiner

*Primary Examiner* — Sujoy Kundu
*Assistant Examiner* — L. Anderson
(74) *Attorney, Agent, or Firm* — Robert H. Earp, III (57) ABSTRACT

A system and method for determining a change in a thickness and temperature of a surface of a material are disclosed herein. The system and the method are usable in a thermal protection system of a space vehicle, such as an aeroshell of a space vehicle. The system and method may incorporate micro electric sensors arranged in a ladder network and capacitor strip sensors. Corrosion or ablation causes a change in an electrical property of the sensors. An amount of or rate of the corrosion or the ablation and a temperature of the material is determined based on the change of the electrical property of the sensors.

19 Claims, 7 Drawing Sheets

MATERIAL DAMAGE SYSTEM AND METHOD FOR DETERMINING SAME

ORIGIN OF THE INVENTION

The invention described herein was made by employees of the United States Government and may be manufactured and used by or for the Government for Government purposes without the payment of any royalties thereon or therefore.

BACKGROUND OF THE DISCLOSURE

Damage to materials due to use and environmental conditions is problematic in many industries. Corrosion, ablation and erosion are examples of material damage that effect industrial applicability and use resulting in increased maintenance costs, compromised safety, higher production costs and other negative results. In order to mitigate this damage, corrosion monitoring is necessary.

In the aeronautical industry, for example, thermal protection systems are critical for the protection of space vehicles and payloads during re-entry. The thermal protection system is usually attached to the entire front surface of the aero-shell that bears the major blunt of atmospheric re-entry. The mission success of the space vehicle is fundamentally dependent on the thermal protection system material protecting the aero-shell from the aggressive conditions encountered during entry. Several entry conditions (e.g. radiation, shock and ionization) combine to ablate the thermal protection system material and their effects increase as the anticipated size and mass of future vehicles destined for planets with atmosphere increases. It is, therefore, important to determine the temperature and rate at which the thermal protection system material recedes toward the aero-shell due to ablation.

The current state of the art of instrumentation of the thermal protection system uses conventional thermocouples and resistors to sense temperature and resistance, respectively. These thermocouples and resistors are manually placed in cylindrical plugs that are made from the temperature protection system material. The plugs are subsequently inserted in holes drilled in the main thermal protection system material that is incorporated into the aero-shell. The purpose of the thermocouples is to measure the temperature spatial and temporal temperature gradient along the trajectory axis of the thermal protection system material and also over the surface of the thermal protection system. The resistor measures the ablation of the char layer of the thermal protections system material. The sensors are embedded in the plug with the thermocouple and then inserted into the main thermal protection system material.

There are several problems with these sensor arrangements. First, these instrumented plugs are time consuming to manufacture and problematic to integrate into a space vehicle. Integration requires machining holes to accommodate these instrumented cylindrical plugs. The cost and time to integrate plugs into a heat shield of the space vehicle can have significant cost and schedule impacts. Presently, insertion and gluing of the plug into the thermal protection system material leaves a circular boundary of homogeneous material discontinuity between the plug and the main thermal protection system. The circular boundary is defined by the glue material. During entry phase, the boundary layer shock/thermal protection system interaction could preferentially ablate this circular boundary section, leading to enhanced turbulence and accelerated ablation. The potential result would be the disgorging of the plug and exposure of the aero-shell, thus compromising the safety of the vehicle. To dramatically reduce the impact of incorporating instrumentation into a thermal protection system of the space vehicle, a new measurement system and methodology is needed.

Second, the plug approach limits the number of thermocouple and resistor carrying plugs that can be positioned in the thermal protection system. Too many plugs, for the purpose of improving area coverage and resolution, could potentially affect the structural and mechanical integrity of the thermal protection system material. It could also increase the number of possible sites for shock induced damage. Also, the manual arrangement of the sensors within the plug severely reduces the number of sensors needed for high resolution profiling of the temperature gradient and the ablation recession rate. Additionally, due to the limited number of sensors, a high resolution, large area tomographic profile of the thermal protection system is impossible to obtain.

It is anticipated that the thermal protection system area will continue to increase with increasing payload, a tomographic profile of the condition of the thermal protection system becomes important in monitoring entry and actively changing the entry axis to avoid risks. Accordingly, to improve thermal protection systems of space vehicles as well as detecting damage to materials of other surfaces, whether caused by corrosion, ablation or the like, a new system and method of use is needed.

SUMMARY OF THE DISCLOSURE

In an embodiment of the disclosure, a system is disclosed having a material susceptible to corrosion or ablation and having a thickness defined between a first end and a second end. The first sensor and a second sensor are on the material and extend along the thickness adjacent the first end and toward the second end. The first sensor has an electrical component that changes an electrical property of the sensor as temperature of the material changes. The second sensor has an electrical property that is substantially constant with respect to changes in temperature of the material. An electrical circuit coupled to the first sensor and the second sensor determines the change in the electrical property of each of the first sensor and the second sensor. A processor determines a thickness and a temperature of the material based on the change of the electrical property of the first sensor and the second sensor.

In another embodiment of the disclosure, a method is disclosed positioning a first micro electric sensor and a second micro electric sensor within a susceptible material. The method further includes applying a current or voltage to the first micro electric sensor and the second micro electric sensor. Furthermore, the method includes exposing the susceptible material to a substance causing a change in a temperature and thickness of the susceptible material. In addition, the method includes determining the temperature of the susceptible material from an electrical property of the first micro electric sensor. Moreover, the method includes determining the thickness of the susceptible material from an electrical property of the second micro electric sensor. The electrical property of the first micro electric sensor changes substantially more with temperature than the second micro electric sensor.

In yet another embodiment of the disclosure, a method is disclosed for embedding a plurality of sensors within a material. The plurality of sensors have at least a first ladder sensor, a second ladder sensor, and a capacitor strip. The second ladder sensor has more rungs than the first ladder sensor. Further, the second ladder sensor has electrical components that are less temperature sensitive than electrical components of the first ladder sensor. The method also includes applying a current or voltage to each of the plurality of sensors, and exposing the material to a change in temperature causing a change in an electrical property of at least the second ladder sensor. Furthermore, the method includes ablating a portion of the material to change an electrical property of at least the first ladder sensor and the capacitor strip. Still further, the method includes determining a temperature of the material based on the change in the electrical property of the first ladder sensor and the second ladder sensor. Moreover, the method includes determining a thickness of the material based on the change of the electrical property of the capacitor strip and the change of the electrical property of the second ladder sensor.

DETAILED DESCRIPTION OF EMBODIMENTS OF THE DISCLOSURE

Embodiments of the present disclosure generally describe a system and method for determining temperature and/or thickness of a surface of a susceptible material. The susceptible material may be susceptible to a change in thickness by exposure to extreme temperatures, radiactive sources, corrosive substances, or other sources that may damage the surface of and/or structure of the susceptible material. While embodiments of the present disclosure are described as being implemented with a sensor having a ladder network, the present disclosure should not interpreted as limited as requiring the use of a ladder network. The present disclosure describes sensors that may be implemented within the spirit of the invention that are not arranged in a ladder network.

In addition, the present disclosure should not be deemed as limited to use on a space vehicle or in the aerospace industry. Those having ordinary skill in the art will appreciate that the present disclosure has various applications in many industries. For example, the embodiments disclosed herein have broad applications across any industry where it is desirous to determine corrosion, erosion, ablation, recession, and surface temperature of a material.

In at least some embodiments, the present disclosure provides temperature and recession rate measurements of a susceptible material. For example, the present disclosure may utilize or employ a sensor comprising an electrical circuit having components the cause a change in an electrical property upon corrosion, ablation or a change in temperature of the susceptible material.

Figure 1:
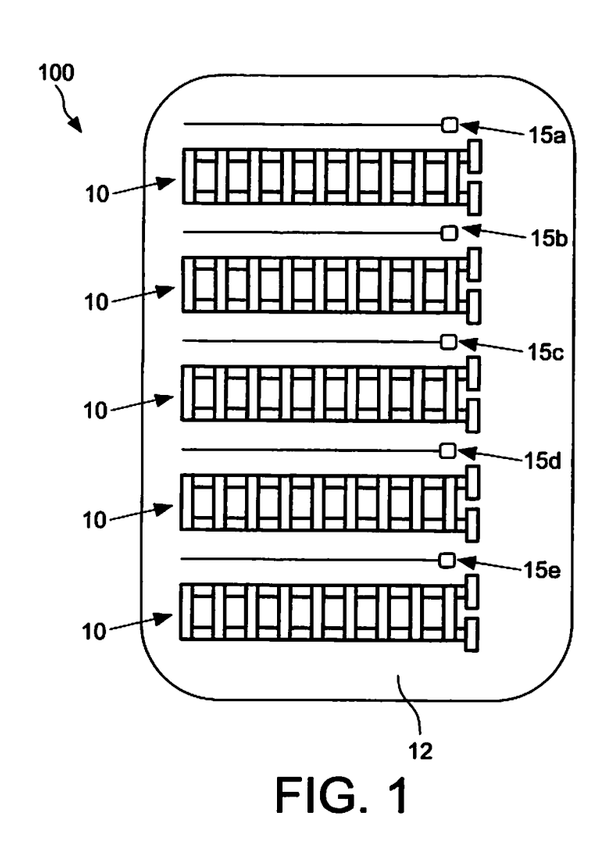
FIG. 1 illustrates a plurality of sensors on a material in an embodiment of the present disclosure.

FIG. 1 illustrates an embodiment of a system 100 comprised of a plurality of sensors 10 and a plurality of sensors 15a-15e arranged on a substrate 12. The system 100 may utilize the substrate 12 in order to fabricate the sensors 10, 15a-15e. For example, the system 100 may be a micro electromechanical system ("MEMS") whereby the sensors 10, 15a-15e are micro electric sensors. In such an embodiment, the substrate 12 may be used to fabricate one or more of the sensors 10, 15a-15e.

As one example of fabricating the sensors 10, 15a-15e, the substrate 12 may be selectively removed in order to realize miniaturized components. Such micromachining may be accomplished using chemical or physical means. For example, a bulk micromachining technique may be used, such as chemical wet etching that involves immersion of a substrate, such as the substrate 12, into a reactive chemical solution. As a result of immersion in the reactive chemical solution, the exposed regions of the substrate 12 may be etched at measurable rates. Chemical wet etching may be used to provide a relatively high etch rate and permit selective etching.

Surface micromachining is another method that may be used for the fabrication sensors 10, 15a-15e on the substrate 12 in an embodiment where the sensors 10, 15a-15e are micro electric devices or MEMS devices. Generally, surface micromachining may involve deposition of a film material to act as a temporary mechanical layer onto which the actual device layers are built. Next, a structural layer may be deposited and patterned on the film material followed by the removal of the temporary layer to release the mechanical structure layer from the constraint of the underlying layer. As a result, the structural layer may be freed. One of the reasons surface micromachining may be used is that it provides for precise dimensional control.

A person having ordinary skill in the art will appreciate many methods of fabricating the sensors 10, 15a-15e. The invention should not be deemed as limited to any specific fabrication technique. In addition, the sensors 10, 15a-15e being micro electric sensors and/or MEMS sensors are an embodiment and the disclosure is not limited thereto.

As shown in FIG. 1, each of the sensors 10 may have a plurality of electrical components 14a-14i, 16a-16h, and 18a-18h. One or more of the sensors 15a-15h may be positioned adjacent each of the sensors 10. In an embodiment, the sensors 15a-15h each have a capacitor strip configured to ablate, recess or otherwise have its length change in response to ablation, recession, corrosion or erosion of the thickness of the substrate 12. In such an embodiment, the capacitor strip may comprise a pair of opposing electrodes, a pair of electric wires, a coaxial cable, micro sized capacitors positioned in series or in parallel, a single wire, a pair of opposing plates, or any type of capacitive device that will change its capacitance with length or surface area. The sensors 15a-15h may not be temperature dependent such that any change in the temperature of the substrate 12 will have substantially zero effect on electrical properties of the sensors 15a-15h. Accordingly, the sensors 15a-15h may be positioned into a device to measure changes in dimension, such as changes in a thickness of the substrate 12.

Figure 2:
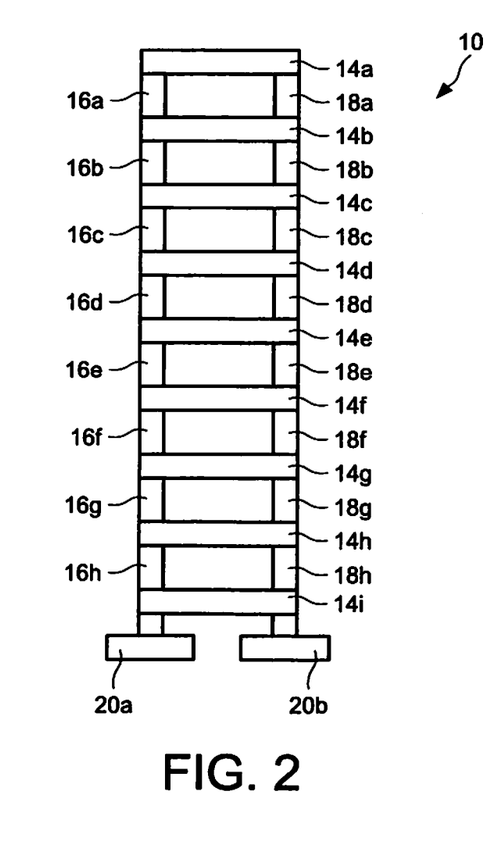
FIG. 2 illustrates a sensor in an embodiment of the disclosure.

FIG. 2 illustrates the sensor 10 having the plurality of electrical components 14a-14i, 16a-16h, and 18a-18h that may be used in the system 100. The electrical components 14a-14l, 16a-16h, and 18a-18h of the sensor 10 may be in electrical communication to form an electrical network. The electrical components 14a-14i, 16a-16h, and 18a-18h may comprise conducting lines, conducting wires, resistors, and/or inductors. The electrical components 14a-14i, 16a-16h, and 18a-18h may be in parallel or in series as shown in FIG. 2. In an embodiment, each of the electrical components 14a-14i, 16a-16h, and 18a-18h has at least one resistor or inductor. The electrical components 14a-14i, 16a-16h, and 18a-18h may have at least one resistor, or inductor in addition to or alternative to a conducting line or wire.

The arrangement of the electrical components 14a-14l, 16a-16h, and 18a-18h may be in a ladder network configuration as shown in FIG. 2. The ladder network configuration may permit a portion of the electrical components 14a-14i, 16a-16h, and 18a-18h to become electrically separated while permitting electrical communication between the other portion of the electrical components 14a-14i, 16a-16h, and 18a-18h to terminals 20a, 20b, as shown in FIG. 2. As an example, the electrical component 14a may be removed, may be destroyed, or may otherwise be electrically separated from the other electrical components 14b-14i, 16a-16h, and 18a-18h. Electrically disconnecting the electrical component 14a, for example, may change a resistance, or a current in the sensor 10. Conversely, a break, ablation or the like in the sensor 15 may change the capacitance to correspond with a new thickness of the eroding material.

As mentioned, the electrical components 14a-14i, 16a-16h, and 18a-18h may be electrically connected to the terminals 20a, 20b, as shown in FIG. 2. As a portion of the electrical components 14a-14i, 16a-16h, and 18a-18h are electrically separated from the electrical network, the resistance or the current as measurable from the terminals 20a, 20b may change.

In addition, the electrical components 14a-14i, 16a-16h, and 18a-18h may be temperature sensitive such that a change in a temperature of at least one of the electrical components 14a-14i, 16a-16h, and 18a-18h causes a change in the electrical property of the sensor 10. The electrical components 14a-14i, 16a-16h, and 18a-18h may have a positive or negative temperature coefficient. In the case of a positive temperature coefficient, a resistance or capacitance of one or more of the electrical components 14a-14l, 16a-16h, or 18a-18h, may increase with an increase in temperature. On the other hand, a negative temperature coefficient results in a decrease in resistance or capacitance as temperature increases. It should also be noted that a zero temperature coefficient is also a possible coefficient of the electrical components 14a-14i, 16a-16h, and 18a-18h.

Figure 3:
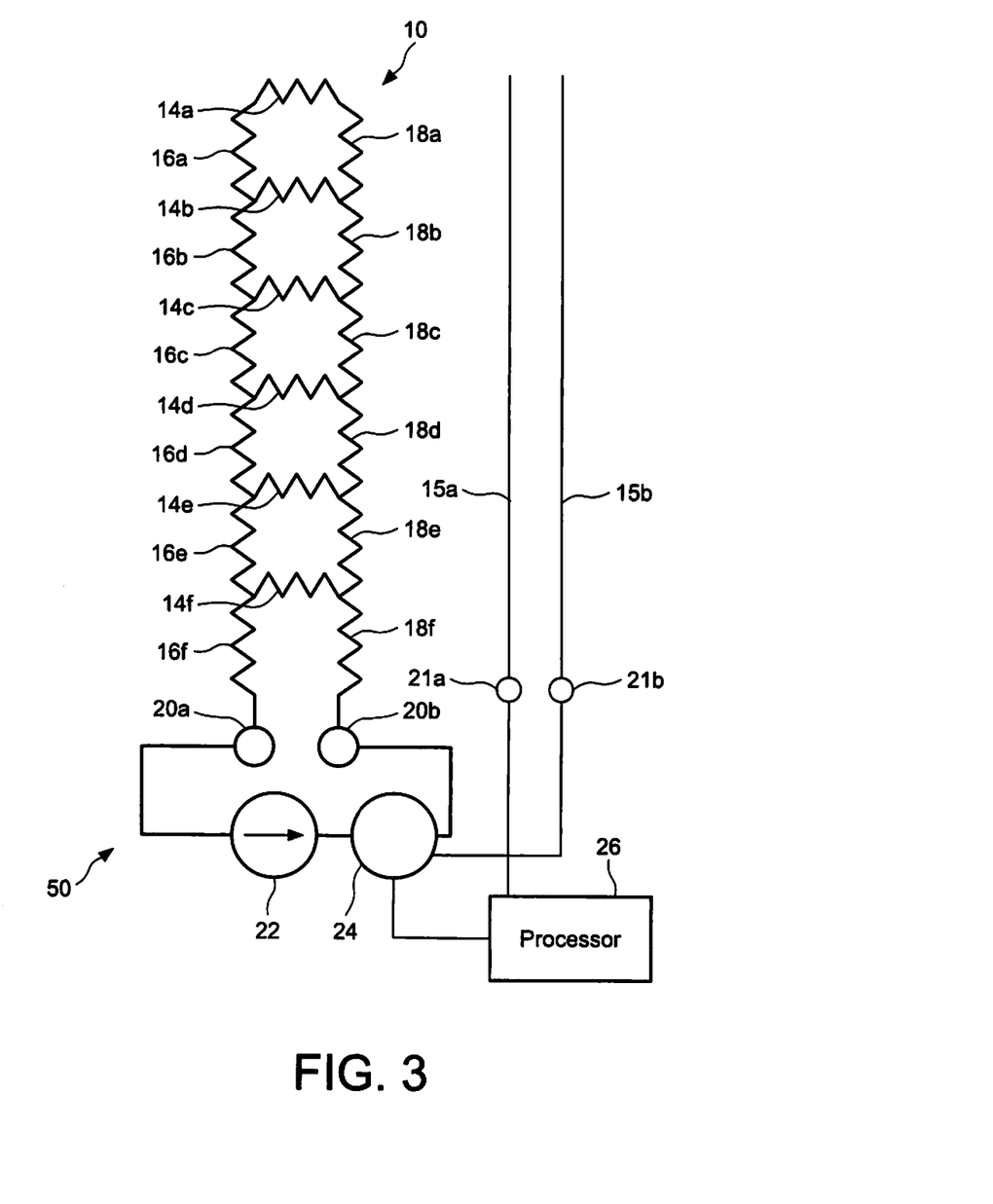
FIG. 3 illustrates a sensor connected to a sensing device, source and processor in an embodiment of the disclosure.

FIG. 3 illustrates an embodiment of the sensor 10 and the sensors 15a, 15b. For explanatory purposes, the electrical components 14a-14f, 16a-16f, and 18a-18f are shown as each having a resistor. The electrical components 14a-14f, 16a-16f, and 18a-18f are connected to the terminals 20a, 20b and arranged in a ladder network. The electrical component 16f is electrically connected to the terminal 20a and may extend substantially parallel to the electrical component 18f, which is electrically connected to the terminal 20b. The electrical component 14f is electrically connected to the electrical components 16f, 18f. The electrical component 14f may be substantially perpendicular to the electrical components 16f, 18f. The electrical components 16e and 18e may be electrically connected to the electrical components 14f, 16f, 18f and extend away from the terminals 20a, 20b. The other electrical components 14a-14e, 16a-16e, and 18a-18d may be electrically connected in a similar manner as shown in FIG. 3.

The sensors 15a, 15b extend in a direction substantially parallel to the sensor 10. The sensors 15a, 15b may, in an embodiment, each comprise a wire, a semiconductor, a doped ceramic, or a plate for storing a charge. In another embodiment, each of the sensors 15a, 15b may comprise a pair of wires, a pair of plates or one or more devices positioned along its length for storing a charge. The sensors 15a, 15b may be configured such that a change in its length will change an electrical property of the sensors 15a, 15b. The change in the electrical property may be related to a change in the length of sensors 15a, 15b.

Figure 4:
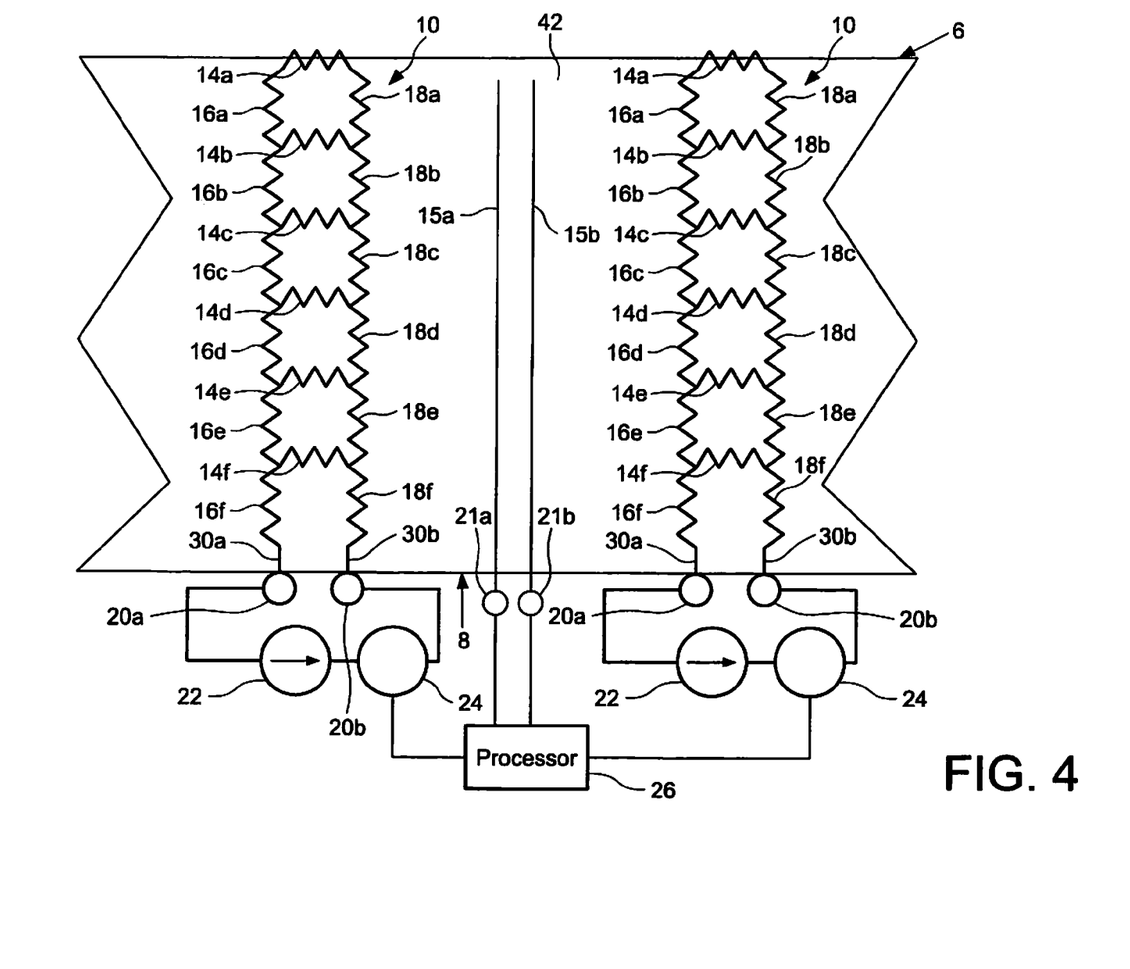
FIG. 4 illustrates a first sensor and a second sensor connected to a processor in an embodiment of the disclosure.
Figure 5:
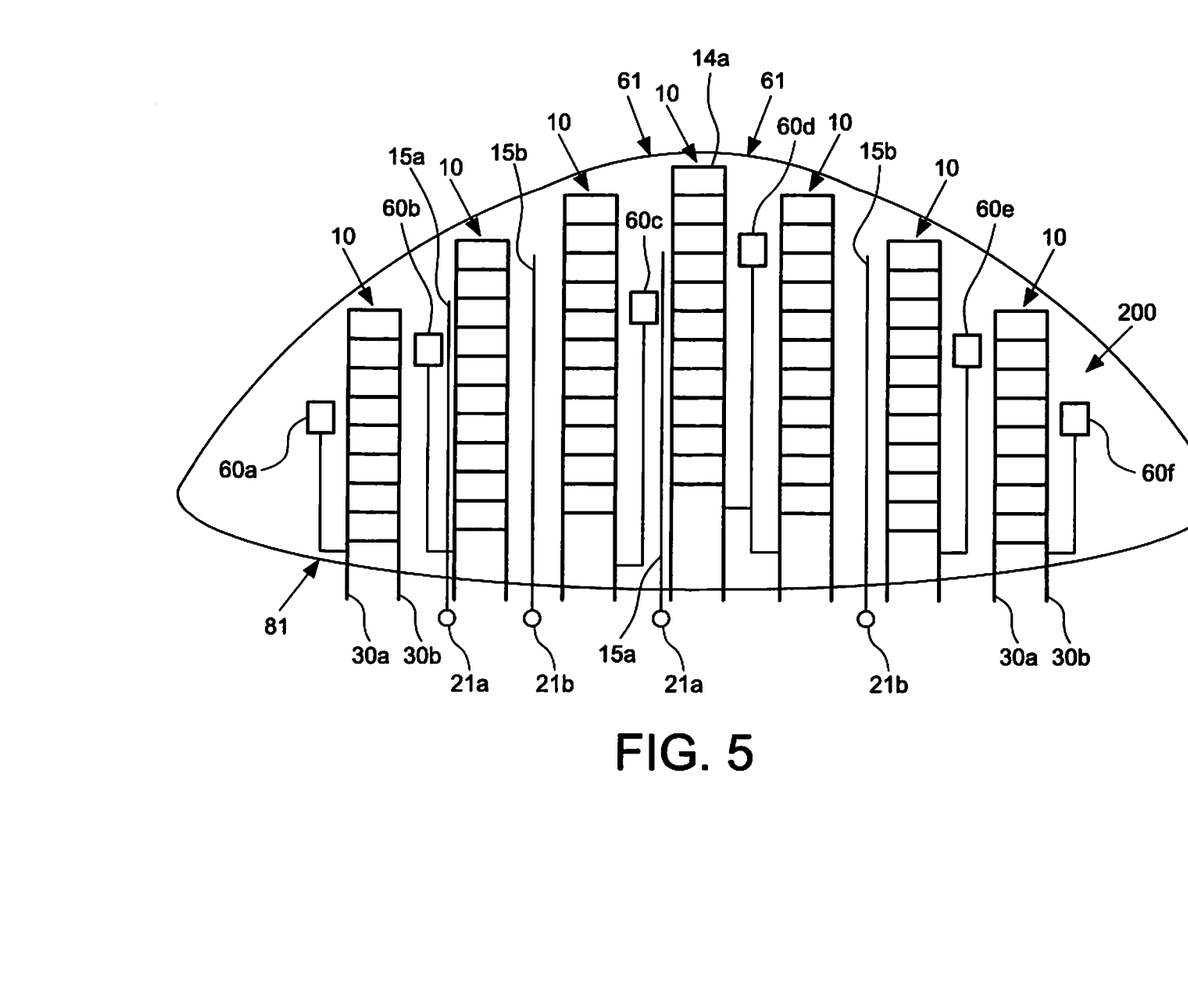
FIG. 5 illustrates a plurality of sensors within a material in an embodiment of the present disclosure.

An electric circuit 50 is connected to the sensor 10 via the terminals 20a, 20b. The electrical circuit 50 is electrically connected to the electrical components 14a-14f, 16a-16f, and 18a-18f, via the terminals 20a, 20b. For example, as shown in FIGS. 4 and 5, conducting lines 30a, 30b may extend from each of the sensors 10 out of the second end 8 of the susceptible material 42 and connect to the terminals 20a, 20b. The electrical circuit 50 may be electrically connected to the sensor 10 via the terminals 20a, 20b. The electrical circuit 50 may also be connected to the sensors 15a, 15b via terminals 21a, 21b. Several other alternative series/parallel connections exist, but the above is for illustrative purposes.

The electrical circuit 50 may comprise an electrical energy source 22 electrically connected to the terminals 20a, 20b and/or the terminals 21a, 21b. The electrical energy source 22 may deliver a current and/or a voltage to the sensor 10 and/or the sensors 15a, 15b. For example, the electrical energy source 22 may deliver a constant voltage or a constant current to the sensor 10, such as the electrical components 14a-14f, 16a-16f, and 18a-18f, via the terminals 20a, 20b. In the case of constant voltage, a change in a resistance of one of the electrical components 14a-14f, 16a-16f, and 18a-18f results in a change in the current passing through the electric circuit 50. An increase in a resistance, results in a lower current, while a decrease in resistance results in an increased current. The electrical energy source 22 may also deliver a voltage or current to the sensors 15a, 15b. In an embodiment where the sensors 15a, 15b are capacitors, a change in length of the sensors 15a, 15b may change an electrical property of the sensors 15a, 15b. For example, as the length of the sensors 15a, 15b decrease, a capacitance of the sensors 15a, 15b may decrease.

The electrical circuit 50 may have a measuring device 24 to measure an electrical property of the electrical circuit 50, the sensor 10 and/or the sensors 15a, 15b. The measuring device 24 may be positioned between the terminals 20a, 20b. The measuring device 24 or a second measuring device (not shown) may be in electrical communication with the terminals 21a, 21b of the sensors 15a, 15b. The measuring device 24 may determine and/or may measure a current or voltage of the sensor 10 and the sensors 15a, 15b. In an embodiment, the measuring device 24 may be an ammeter, or digital meter, to measure and/or determine an amount of current passing therethrough. The measuring device 24 may instead or in addition to current measure voltage.

A processor 26 may be electrically connected to the measuring device 24 to receive measurement data from the measuring device 24. FIG. 4 illustrates an embodiment of the processor 26 connected to the measuring device 24 of each of the sensors 10. The processor 26 may also be in communication with terminals 21a, 21b of the sensors 15a, 15b. In this embodiment, the terminals 21a, 21b may contain and/or may incorporate a measuring device for determining an electrical property of the sensors 15a, 15b, such as current, voltage or capacitance. The terminals 21a, 21b may communicate the electrical property to the processor 26 for determination of a length of the sensors 15a, 15b. The processor 26 may be positioned locally or remotely with respect to the electrical circuit 50 and the sensor 10.

FIG. 4 also illustrates the sensors 10, 15a, 15b positioned between a first end 6 and a second end 8 of a susceptible material 42. The susceptible material 42 may be any material or device in which corrosion, ablation, erosion and/or surface temperature determination may be advantageous. Non-limiting examples of the susceptible material 42 include a braking material for a vehicle, a thermal protection system of a space vehicle, or a fluid conduit. A circuit method of multiplexing can be used to connect numerous sensors 10, 15a, 15b so that sampling, such as high speed sampling, may be used to interrogate a plurality of the sensors 10, 15a, 15b to allow for a real-time, or substantially real-time, topographic display of the erosion on a display (not shown).

The thickness of the susceptible material 42 may be defined between the first end 6 and the second end 8. The first end 6 of the susceptible material 42 may be positioned adjacent to and/or exposed to a substance that may cause a change in the thickness of the susceptible material 42. For example, the substance causing a change in thickness of the susceptible material 42 may be a fluid at an extreme temperature, a radiative substance, a corrosive substance, or other substance that may cause a change in the thickness of the susceptible material, 42, such as by damage to the surface of and/or structure of the susceptible material 42.

The substance may change the thickness of the susceptible material 42 causing separation of a portion of the sensor 10 from a remaining portion of the sensor 10 and a change in length of the sensors 15a, 15b. For example, the substance may decrease the thickness of the susceptible material 42 and electrically separate one or more of the electrical components 14a-14f, 16a-16f, and 18a-18f, such as the electrical component 14a, from the sensor 10. Additionally, the substance may decrease the thickness of the susceptible material 42 and electrically separate a portion of the sensors 15a, 15b and/or decrease a length of the sensors 15a, 15b. As a result, the measuring device 24 may measure a change in the electrical property of the electrical circuit 50, such as a change in the current. In an embodiment, upon electrical separation of the electrical component 14a, the current measured at the measuring device 24 may decrease due to an increased resistance of the electrical circuit 50, if, for example, the electrical component 14a is a resistor. If, for example, the sensors 15a, 15b are capacitor strips, a decrease in length of the sensors 15a, 15b may decrease a capacitance. The processor 26 may be in electrical and/or data communication with the measuring device 24 to relate a change in the electrical property of the sensor 10 and the sensors 15a, 15b to a change in the thickness of the susceptible material 42. In an embodiment, the processor 26 may compare a computed change in thickness of the susceptible material 42 from the sensors 10 with a computed change in thickness of the susceptible material 42 from the sensors 15a, 15b.

Turning again to FIG. 4, the substance changing the thickness of the susceptible material 42 may cause a greater change to the susceptible material 42 at one of the sensors 10, 15a, 15b than one of the other sensors 10, 15a, 15b. In such an event, the processor 26 may receive data and/or communication from the measuring device 24 and determine the thickness of the susceptible material 42 at each of the sensors 10, 15a, 15b. Advantageously, the sensors 10, 15a, 15b may be spaced at predetermined locations to measure a change of thickness, such as due to corrosion or ablation. While FIG. 4 only illustrates two of the sensors 10, any number of the sensors 10 may be positioned at predetermined locations along the susceptible material 42 resulting in information related to the thickness at each location of each of the sensors 10.

In addition to the change of thickness of the susceptible material 42, the sensor 10 may determine a temperature of the susceptible material 42. The change in temperature of the susceptible material 42 may cause a change in temperature of one or more of the electrical components 14a-14f, 16a-16f, and 18a-18f. As the temperature of one of the electrical components 14a-14f, 16a-16f, and 18a-18f changes, an electrical property of the sensor 10 changes. For example, the electric property of the sensor 10 may be a resistance or capacitance that may change with temperature. The change in the capacitance of resistance of the sensor 10 may be the result of the change in temperature. Changing the electrical property may result in a change in current passing through the sensor 10 and/or current at the measuring device 24.

As set forth above, the change in the temperature and the change in the thickness of the susceptible material 42 may cause a change in the electrical property of the sensor 10. The processor 26 may determine the change in the electrical property due to the temperature and the change in the electrical property due to the change in thickness of the susceptible material 42. The processor 26 may have information and/or may determine a relationship of the electrical property of each of the electrical components 14a-14f, 16a-16f, and 18a-18f and temperature. In addition, the processor 26 may have information and/or may determine a relationship of the electrical property of each of the electrical components 14a-14f, 16a-16f, and 18a-18f and a change in the thickness of the susceptible material 42. The measuring device 24 and/or the processor 26 may determine a change in the electrical property of the sensor 10. As mentioned, the change in the electrical property of the sensor 10 may be a change in current, voltage or the like. The processor 26 may then determine the change in electrical property due to the temperature change and the change in the electoral property due to the change in thickness of the susceptible material 42.

As in the example of FIG. 4, the electrical components 14a-14f, 16a-16f, and 18a-18f may be resistors. If these resistors have a negative temperature coefficient, an increase in temperature of the electrical components 14a-14f, 16a-16f, and 18a-18f may cause a decrease in resistance. Simultaneously if the increase in temperature causes a decrease of thickness of the susceptible material 42 by ablating a portion of the susceptible material 42 and the electrical component 14a, then the resistance of the sensor 10 may increase. The measuring device 24 may measure a change in current as a result of the change in resistance. For explanatory purposes, if the overall resistance increases, then the current at the measuring device 24 may decrease. However, the current at the measuring device 24 may be higher than expected if the electrical component 14a is separated from electrical communication with the other electrical components 14b-14f, 16a-16f, and 18a-18f. The current may be higher than expected as the temperature increase may cause the resistance in the other electrical components 14*b*-14*f,* 16*a*-16*f,* and 18*a*-18*f* to decrease. The processor 26 may determine the change of thickness of the susceptible material 42 and the change in temperature of the susceptible material 42 due to the decrease in the current.

As another example, the sensors 10 as shown in FIG. 4 may be arranged such that any change in thickness of the susceptible material 42 at one of the sensors 10 will cause the same or a substantially similar change in thickness of the susceptible material 42 at the other sensor 10. In order to separate the change in electrical property due to temperature from the change in electrical property due to the change in thickness, one of the sensors 10 may have the electrical components 14*a*-14*f,* 16*a*-16*f,* and 18*a*-18*f* that do not change with temperature. In yet another embodiment, one of the sensors 10 may have the electrical components 14*a*-14*f,* 16*a*-16*f,* and 18*a*-18*f* with positive temperature coefficients and the other sensor 10 may have the electrical components 14*a*-14*f,* 16*a*-16*f,* and 18*a*-18*f* with negative temperature coefficients. The electrical components 14*a*-14*f,* 16*a*-16*f,* and 18*a*-18*f* of the sensors 10 may have the same number of resistors, capacitors and electrical conductors such that the sensors 10 are similar. Alternatively, the sensors 10 may have a distinct number, type, location and/or arrangement of the electrical components 14*a*-14*f,* 16*a*-16*f,* and 18*a*-18*f*. In either case, the processor 26 may utilize this information to determine a change in thickness of the susceptible material 42 and/or a temperature of the susceptible material 42. These embodiments are not mutually exclusive and may be used in combination in order to determine temperature and thickness of the susceptible material 42 at each of the sensors 10.

In an embodiment, the sensors 15*a,* 15*b* may be used to determine a change in thickness of the susceptible material 42. In order to ensure accurate measurement of the change in thickness, the sensors 15*a,* 15*b* may not vary with temperature. Accordingly, the entire change, or at least a substantial amount of the change, in electrical property of the sensors 15*a,* 15*b* may be attributed to a change in thickness of the susceptible material 42. Again, the processor 26 may determine the change in thickness of the susceptible material 42 based on the change in the electrical property of the sensors 15*a,* 15*b*. The temperature of the susceptible material 42 may be determined from the sensors 10, such as by the processor 26 computing the temperature based on a change in the electrical property of the sensor 10. Accordingly, a temperature and thickness of the susceptible material 42 may be determined. The temperature and thickness of the susceptible material 42 may be determined along an entire surface to generate a tomographic image of the susceptible material 42.

In addition to utilizing the sensor 10 to determine the temperature of the susceptible material 42, the change in thickness of the susceptible material 42 may be determined from a change in electrical property of the sensor 10. The processor 26 may determine the change in thickness of the susceptible material 42 from the sensor 10 and the sensors 15*a,* 15*b* independently or using a combination. In the event these are independently measured, the values may be compared and resolved to improve accuracy, such as by determining the likelihood of each measurement. It may be determined that one of the sensors 10, 15*a,* 15*b* is more accurate at certain temperature ranges than at other temperature ranges.

As another example, one could assume that the sensors 10 of FIG. 4 are spaced such that properties of the susceptible material 42 are identical or substantially similar at each location of a first sensor 10 and a second sensor 10. For example, the thickness and temperature of the susceptible material 42 at the first sensor 10 may not differ much, if at all, from the thickness and temperature of the susceptible material 42 at the second sensor 10. The processor 26 may determine the thickness, the rate of thickness change, and/or the temperature of the susceptible material 42 of each of the sensors 10 independently. If, for example, the first sensor 10 does not vary its electrical property with temperature while the second sensor 10 does vary with temperature, then the processor 26 may determine the amount of change of the electrical property due to temperature. The change in the electrical property due to temperature may then be correlated to a thickness or a change in thickness of the susceptible material 42. Similarly, the sensors 10 may be used to independently compute the thickness of the susceptible material 42 to compare and improve the measurement. Use of the sensors 10 along or within the susceptible material 42 may permit the processor 26 to generate a tomographic image or other representation of the temperature and/or a tomographic image of the thickness (or change of the thickness, such as ablation, erosion, corrosion or the like) of the susceptible material 42.

FIG. 5 illustrates an embodiment of the disclosure of the sensors 10, 15*a,* 15*b* embedded into a thermal protection system 200 of a space vehicle, such as a heat shield of an aeroshell. The thickness of the aeroshell 200 is defined by a first end 61 and a second end 81. The sensors 10, 15*a,* 15*b* may be micro scale sensors fabricated in materials that are compatible with the material of the thermal protection system 200. Any numbers of the sensors 10, 15*a,* 15*b,* such as hundreds, are fabricated in the substrate 12 and may be released into the material prior to final forming of the thermal protection system 200. In an embodiment, at least one of the sensors 15*a,* 15*b* may be used for each of the sensors 10. For example, each of the sensors 10 may have at least one of the sensors 15*a,* 15*b* positioned adjacent thereto. Each of the sensors 10, 15*a,* 15*b* and/or each of the substrates 12 may be positioned transversely in strategic locations of the thermal protection system 200 before final casting, molding, or compression. In an embodiment, the sensors 10, 15*a,* 15*b* are positioned so that each of the sensors 10, 15*a,* 15*b* extends along the thickness of the thermal protection system 200. Each of the conducting lines 30*a,* 30*b* may be connected to terminals 20, 20*b* as shown in FIGS. 2-4. In the case of the thermal protection system 200, the conducting lines 30*a,* 30*b* are extending out of a cold end, the second end 81, of the thermal protection system 200. In other words, the first end 61 is generally the end exposed to high temperatures during reentry. The conducting lines 30*a,* 30*b* and the terminals 21*a,* 21*b* of the sensors 15*a,* 15*b* are subsequently connected to an electronic circuit, such as the electric circuit 50 shown in FIGS. 3 and 4, that is used to generate a tomographic image of the surface temperature and recession rate of the thermal protection system 200. The processor 26 may be connected. The processor 26 may be connected to transfer data or information from the thermal protection system 200 to other locations of the space vehicle.

Thermoelectric devices 60*a*-60*f* may be embedded or otherwise positioned in the thermal protection system 200. It should be understood that the thermoelectric devices 60*a*-60*f* may be located on and/or may be embedded in the substrate 12. The thermoelectric devices 60*a*-60*f* (as well as the other features of the thermal protection system 200) may be used with, in addition to and/or as an alternative to features of the aforementioned embodiments of the disclosure.

The thermoelectric devices 60a-60f may scavenge thermal energy of the thermal protection system 200. For example, during reentry to Earth, the space vehicle and, in turn, the thermal protection system 200 may encounter extremely high temperatures permitting thermal energy to be converted to electrical energy by the thermoelectric devices 60a-60f. The thermoelectric devices 60a-60f may be electrically connected to one or more of the sensors 10, 15a, 15b to provide power or current to the sensors 10, 15a, 15b. As shown in FIG. 5, the thermoelectric devices 60a-60f may be positioned at different locations along the thickness of the aeroshell so that ablation of the aeroshell may not eliminate at least some of the thermoelectric devices 60a-60f. The thermoelectric devices 60a-60f may generate sufficient power for one or more of the sensors 10, 15a, 15b. The thermoelectric devices 60a-60f may be in thermal contact with the heat source and thermally insulated from a heat sink by a cavity, for example, in the substrate 12, or other thermal insulation device in the thermal protection system 200.

Figure 6A:
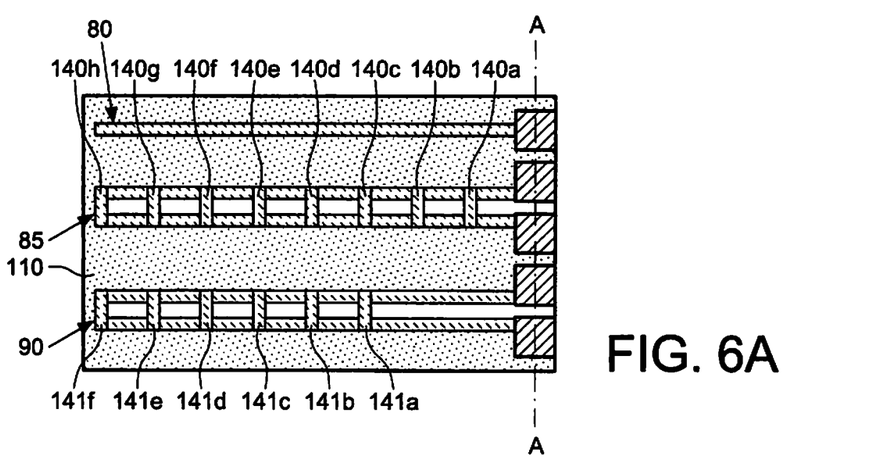
FIG. 6A illustrates a first sensor, a second sensor, and a third sensor on a material in another embodiment of the present disclosure.

FIG. 6A illustrates another embodiment of a substrate 110 having a first sensor 80, a second sensor 85, and a third sensor 90. The substrate 110 may be susceptible to corrosion, ablation and/or temperature changes. The substrate 110 may have qualities and features similar to the substrate 12. A first sensor 80 may be positioned on and/or etched into the substrate 110. In an embodiment, the first sensor 80 may be substantially resistant to temperature changes. For example, the properties of the first sensor 80 may be substantially constant with respect to temperature. As a non-limiting example, the first sensor 80 may be a capacitor strip providing a decrease in capacitance as the first sensor 80 is shortened, such as by ablation, corrosion or the like. To this end, the first sensor 80 may provide a measurement related to ablation or other change in thickness of the substrate 12, 110 and/or the susceptible material 42. The measurement from the first sensor 80 may be a capacitance that relates to a dimension of the first sensor 80, the substrate 12, 110 and/or the susceptible material 42. For example, the measurement may indicate that a length of the first sensor 80 has decreased, indicating corrosion or ablation of the susceptible material 42.

Figure 6B:
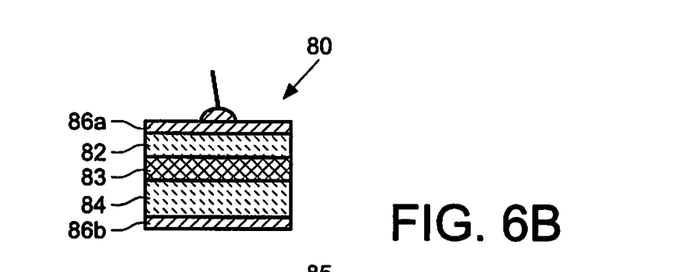
FIG. 6B illustrates a cross-sectional view of the first sensor along the line A-A as shown in FIG. 6A.

The first sensor 80 may comprise a first electrode 82 and a second electrode 84 as shown in FIG. 6B. A dielectric 83 may separate the first electrode 82 from the second electrode 84. The dielectric 83 may be, for example, an electric insulator or any substance capable of substantially preventing electrical charges from passing therethrough. The dielectric 83 defines the gap or separation between the first electrode 82 and the second electrode 84, which of course may be customized based on application. A potential difference may be created across the first electrode 82 and the second electrode 84. The surface area of the first electrode 82 and the second electrode 84 may decrease as corrosion or ablation occurs on the substrate 110 and/or the susceptible material 42. As a result, in an embodiment where the first sensor 80 is a capacitor, the decrease in surface area of the electrodes 82, 84 decrease a capacitance.

Bondpads 86a, 86b may be positioned at opposing sides of the first sensor 80. For example, the bondpads 86a, 86b are positioned on opposite sides of the first electrode 82 and the second electrode 84. The bondpads 86a, 86b may be made of a material that can be incorporated into, attached to and/or secured to the susceptible material 42. The first bondpad 86a may be positioned on the first electrode 82, and the second bondpad 86b may be positioned on the second electrode 84, as shown in FIG. 6B.

Figure 6C:
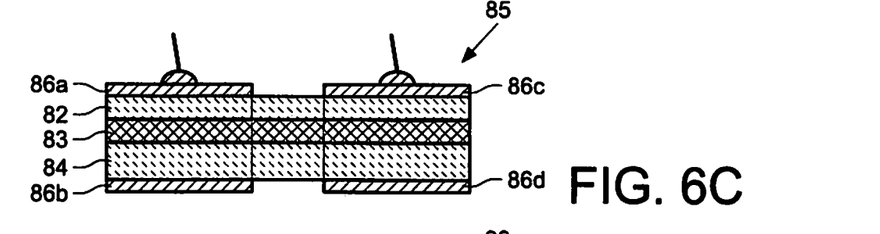
FIG. 6C illustrates a cross-sectional view of the second sensor along the line A-A as shown in FIG. 6A.
Figure 6D:
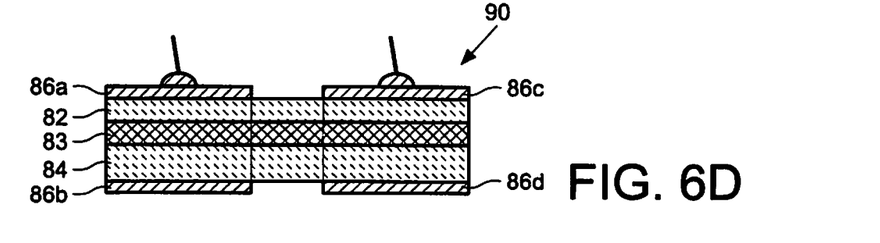
FIG. 6D illustrates a cross-sectional view of the third sensor along the line A-A as shown in FIG. 6A.

FIGS. 6C and 6D illustrate a cross-sectional view of the second sensor 85 and the third sensor 90, respectively. The second sensor 85 and the third sensor 90 may each have bondpads 86a-86d positioned on the first electrode 82 and the second electrode 84, respectively. The bond pads 86c and 86d may be separated a distance from bondpads 86a and 86b. The first electrode 82, the second electrode 84 and the dielectric 83 may extend between the bondpads 86c, 86d and the bond pads 86a, 86b.

The second sensor 85 may have any number of electrical components 141a-141f. In the embodiment shown in FIG. 6A, the second sensor 85 may be utilized to determine an ablation, corrosion or other change in thickness of the substrate 110 and/or the susceptible material 42. As a result, the second sensor 85 may position the electrical components 141a-141f at predetermined positions representative of the degree of measurement of the thickness of the substrate 110 and/or the susceptible material 42 that is desired or required. For example, the electrical components 141a-141f may be positioned such that one of the electrical components 141a-141f is separated from the second sensor 85 at each position or thickness in which it may be beneficial to determine a thickness, ablation or corrosion of the substrate 110 and/or the susceptible material 42.

For example, the second sensor 85 may be arranged as a resistor ladder network where at least a portion of the electrical components 141a-141f is positioned at rungs of the ladder, for example. The separation, disconnection or destruction of a rung of the ladder network changes the electrical properties of the second sensor 85. For example, if the electrical components 141a-141f comprise resistors, one less resistor may be connected to the ladder network as each run of the ladder is destroyed or broken. As each of the electrical components 141a-141f are separated (or destroyed) from the second sensor 85, the resistance of the second sensor 85 may change, such as increase. The change in the electrical property of the second sensor 85 may be substantially related to a change in thickness of the substrate 110 and/or the susceptible material 42. Accordingly, in an embodiment, the electrical components 141a-141f have a minimal change with respect to temperature. As a result, the second sensor 85 may output or measure the ablation or corrosion of the substrate 110 and/or susceptible material 42 with minimal effects on temperature.

The third sensor 90 may be temperature dependent such that an output or measurement of the third sensor 90 changes based on temperature. For example, the third sensor 90 may comprise one or more electrical components 141a-141f that change with respect to temperature. In an embodiment, at least a portion of the electrical components 141a-141f may comprise resistors that change resistance based on temperature. The second sensor 85 may be arranged such that one or more of the electrical components 141a-141f are separated upon ablation or corrosion of the substrate 110. For example, the third sensor 90 may be arranged in a ladder configuration as shown in FIG. 6A where one or more of the electrical components 141a-141f is separated based on ablation or corrosion of the substrate 110. In an embodiment where the third sensor 90 primarily measures temperature and the second sensor 85 primarily measures ablation, the third sensor 90 may have less rungs in the ladder network and/or have electrical components that are more temperature dependent.

The third sensor 90 may have any number of electrical components 141a-141f that may be arranged at predetermined distances along the third sensor 90 in order to cause separation of one or more of the electrical components 141a-141f. Accordingly, any degree of ablation or corrosion may be monitored by positioning the electrical components 141a-141f at predetermined positions.

In an embodiment, the separation (or destruction) of one or more of the electrical components 140a-140h from the second sensor 85 changes the electrical property as does changes in temperature of the second sensor 85. As there may be a number of variables in the changes in the output or measurement of the second sensor 85, the measurement or output of the second sensor 85 may be compared to the output or the measurement from the first sensor 80 and the third sensor 90, and vice versa. In an embodiment where the first sensor 80 is a capacitor strip, the first sensor 80 may provide a relatively accurate measurement of the thickness or the susceptible material 42. This measurement of the thickness of the susceptible material 42 may be used to determine or predict an amount of change in the electrical properties of the second sensor 85 and the third sensor 90 due to the change in thickness. For example, in an embodiment where the second sensor 85 is a resistor ladder sensor, the change in thickness may destroy or otherwise electrically separate one of the resistors causing a change in the electrical property, such as a change in resistance, of the second sensor 85.

As the second sensor 85 and the third sensor 90 may be sensitive to temperature such that electrical properties of the second sensor 85 and the third sensor 90 change with temperature, the electrical properties or measurements of the second sensor 85 and the third sensor 90 may be compared. However, the electrical properties of the second sensor 85 and the third sensor 90 may also change due to ablation or corrosion of the susceptible material 42. In order to determine an amount of change of the electrical properties of the second sensor 85 and the third sensor 90 due to temperature, the measurements may be compared in addition to the measurement of the first sensor 80. The comparison may be an analysis, applying a logic, algorithm or the like using a processor, such as the processor 26.

In an embodiment the first sensor 80, the second sensor 85 and the third sensor 90 may be incorporated into a network whereby numerous sets of the first sensor 80, the second sensor 85 and the third sensor 90. In an embodiment, each set of the sensors 80, 85, 90 may be incorporated into a network or circuit. Each set or each of the sensors 80, 85, 90 may operate similar to a node of a circuit and/or may be connected to a multiplex. The multi-plex may communicate with and interrogate with each sensor and may be addressable to each sensor by using an address of each sensor. A demultiplex may be used to display the sets of sensors 80, 85, 90 as an array on a display. For example, the display may show a temperature and thickness at each node, such as at each set of the sensors 80, 85, 90.

FIGS. 7A-7G illustrate an embodiment of fabricating and/or manufacturing the first sensor 80, the second sensor 85 and the third sensor 90. It will also be appreciated by those having ordinary skill in the art that the embodiment of fabrication and manufacturing methods FIGS. 7A-7G may be utilized for the sensors 10, 15a-15e. It should also be appreciate that the description of the manufacturing and fabrication process is for explanatory purposes, and the present disclosure should not be deemed as limited to this fabrication process or any specific fabrication process.

Figure 7A:
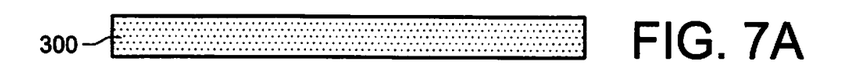
FIGS. 7A-7G illustrate embodiments of steps of manufacturing one or more sensors in an embodiment of the disclosure.

FIG. 7A illustrates a side view of a wafer 300 which may be utilized in an embodiment of the disclosure. The wafer 300 may be, for example, a high resistivity p-type substrate, or a semi-insulating substrate. The wafer 300 of the disclosure should not be deemed as limited to any type of substrate dimensions, but at least in an embodiment may have a thickness of approximately 200 microns. The wafer 300 may be cleaned using a solvent to remove organics, and then the wafer 300 may be dipped in a chemical solution to remove any trace metals, such as a solution of hydrogen peroxide and sulfuric acid. As a non-limiting example, the wafer 300 is dipped into a chemical solution comprising substantially equal volumes of hydrogen peroxide and sulfuric acid for 15 minutes. The wafer 300 may be rinsed, such as by use of de-ionized water. In addition, the wafer 300 may be blown dry with a gas, such as nitrogen.

Figure 7B:
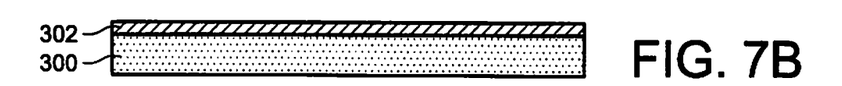

FIG. 7B illustrates deposition of a layer 302 on the wafer 300. The layer 302 may be positioned on the wafer 300 by any process known to those having ordinary skill in the art, including microfabrication techniques, such as sputtering. In an embodiment, the layer 302 may be metallic, such as gold. The layer 302 may then be annealed in a gas, such as nitrogen. For example, the layer 302 may be annealed in nitrogen at 200 degrees Celsius for about thirty minutes. Photoresist or other light sensitive material may be applied on the layer 302 and spun, such as at 3000 revolutions per minute for thirty seconds. Next, the wafer 300 with the layer 302 may be baked at 90 degrees Celsius in a gas, such as nitrogen ambient for a duration, such as five minutes. Next, a bondpad mask is placed over the photoresist and exposed under ultra violet light, such as for ten seconds. The wafer 300 may then be inserted in a developer for about one and a half minutes to develop the photoresist. The wafer 300 may be rinsed in de-ionized, blow dried, and baked again for five minutes in nitrogen ambient at 90 degrees Celsius.

Figure 7C:
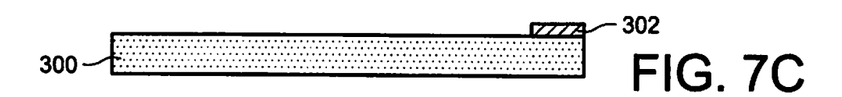
Figure 7D:
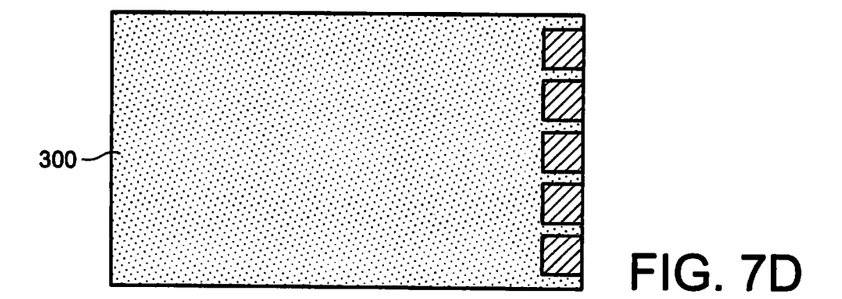

FIG. 7C illustrates that the layer 302 is etched in 10:9:1 volume ratio of $H_2O:HCl:HNO_3$ at 40 degrees Celsius until a portion of the layer 302 is dissolved, leaving only the bondpad gold under the protective photoresist. Next, the photoresist is dissolved in acetone and the wafer and rinsed in de-ionized water. The layer 302 may be one of the bondpads 86a-86d as shown in FIGS. 6B-6D. FIG. 7D illustrates a top view of the wafer 300 of FIG. 7C.

Figure 7E:
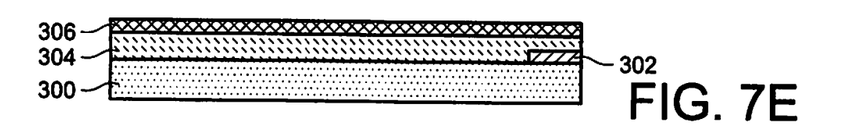

A layer 304 may be deposited on the wafer 300 and the layer 302 as shown in FIG. 7E by any microfabrication technique, such as sputtering. The layer 304 may be an electrode, such as a metal, for example platinum, and may have any dimension, but in this example is approximately 400 nanometers. A silicon or other bonding agent may be deposited on the layer 304 to promote sealing with the layer 306. Next, the layer 306 is deposited by any known microfabrication technique. The layer 306 may be a dielectric material, such as silicon dioxide. The layer 306 may, in an embodiment, be the dielectric 83 as shown in FIGS. 6B-6D.

Figure 7F:
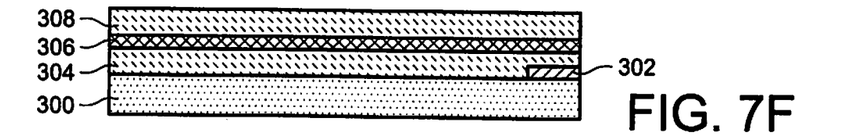

A layer of silicon or other bonding agent is deposited on the layer 306 to promote adhesion. The silicon may be a thin layer, such as 10 nanometers. The layer 308 is then deposited on the layer 306, as shown in FIG. 7F by any known microfabrication technique. The layer 308 may be made of an electrode, such as a metal, for example, platinum. The layer 308 in this embodiment is about three nanometers. The layer 308 may be the electrode 82 as shown in FIGS. 6B-6D.

Figure 7G:
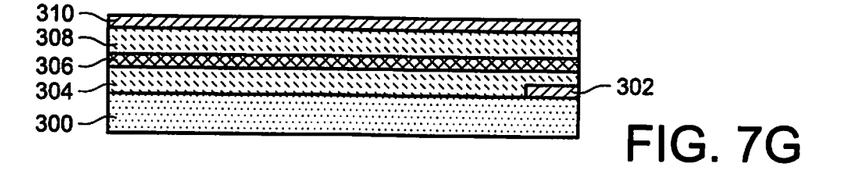

Next, a layer 310 is deposited on the layer 308 using a known microfabrication technique, as shown in FIG. 7G. The layer 310 may be a metallic layer, such as gold. The layer 310 may be about 200 nanometers. Photoresist or other light sensitive material may be applied on the layer 310 and spun, such as at 3000 revolutions per minute for thirty seconds. Next, the wafer 300 with the layer 302 may be baked at 90 degrees Celsius in a gas, such as nitrogen ambient for a duration, such as five minutes. Next, a bondpad mask is placed over the photoresist and exposed under ultra violet light, such as for ten seconds. The wafer 300 may then be inserted in a developer for about one and a half minutes to develop the photoresist. The wafer 300 may be rinsed in de-ionized, blow dried, and baked again for five minutes in nitrogen ambient at 90 degrees Celsius.

Figure 8A:
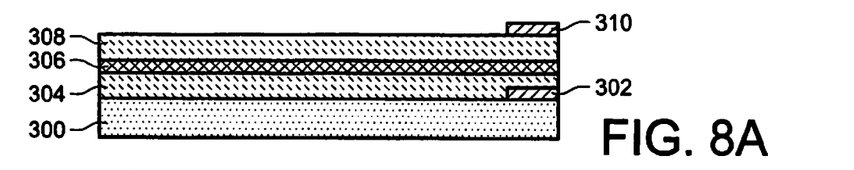
FIGS. 8A-8D illustrate embodiments of additional steps of manufacturing one or more sensors in an embodiment of the disclosure.
Figure 8B:
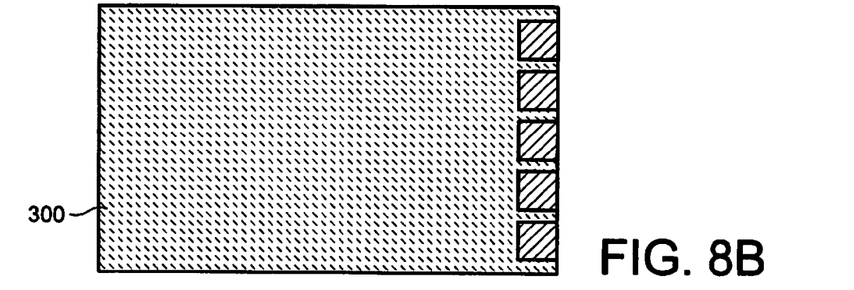

FIG. 8A illustrates that the layer 310 is etched in 10:9:1 volume ratio of $H_2O:HCl:HNO_3$ at 40 degrees Celsius until a portion of the layer 310 is dissolved, leaving only the bondpad gold under the protective photoresist. Next, the photoresist is dissolved in acetone and the wafer and rinsed in de-ionized water. The layer 310 may be one of the bondpads 86a-86d as shown in FIGS. 6B-6D. FIG. 8B illustrates a top view of the wafer 300 of FIG. 8A.

A layer of aluminum may then be deposited on the surface by sputtering or e-beam technique. Photoresist is applied on the aluminum surface and spun at 3000 revolutions per minute for about thirty seconds. After applying the photoresist, the wafer 300 may be baked at 90 degrees Celsius in a gas, such as nitrogen ambient for about five minutes. A sensor element mask may be positioned over the photoresist and exposed under ultra violet light for about ten seconds. The wafer 300 is then inserted in a developer for about one and half minutes to develop the photoresist. The wafer 300 is rinsed in de-ionized, blow dried, and baked again for about five minutes in gas, such as nitrogen ambient, at about 90 degrees Celsius.

Figure 8C:
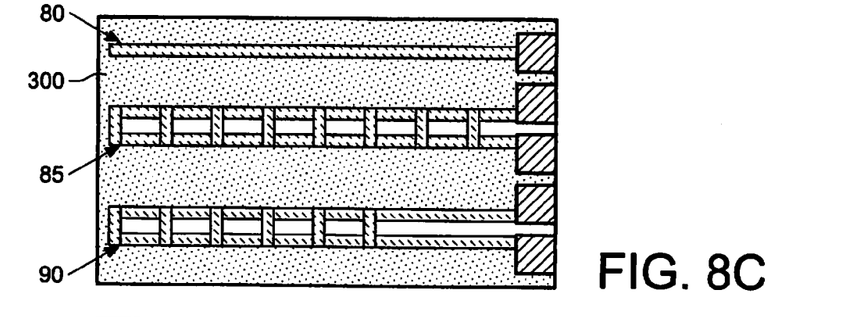
Figure 8D:
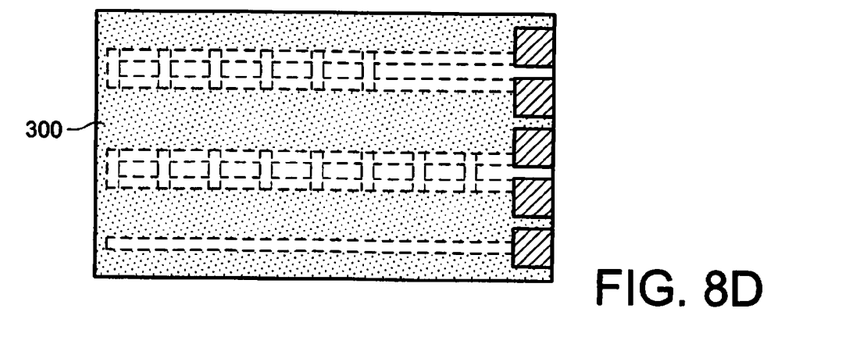

The aluminum layer may be etched using any known etching technique as will be appreciated by those of ordinary skill in the art. For example, the aluminum layer may be etched chemically using phosphoric acid at about 50 degrees Celsius under the field aluminum dissolves substantially or preferably completely, leaving the aluminum under the protective photoresist. To remove the photoresist, acetone may be used to dissolve the photoresist. Then, the wafer 300 may be reinsed in de-ionized water. Using the aluminum as the etch mask, the areas not protected by the aluminum are etched by reactive ion etching method to the wafer 300 as shown in FIG. 8C. The residual aluminum surviving the reactive ion etching is dissolved in phosphoric acid at about 50 degrees Celsius, followed by rinsing with de-ionized water and blowing dry with a nitrogen gas.

The underside of the wafer 300 is etched by reactive ion etching to thin the wafer 300 to at least 100 microns. The front side of the wafer 300 is mounted to a carrier substrate with a thin layer of photoresist and backed at 90 degrees Celsius in nitrogen ambient for about 30 minutes. A seed layer of nickel may be deposited on the backside. Photoresist is applied to the nickel see layer and spun at 3000 revolutions per minute for about 30 seconds. This is followed by baking at 90 degrees Celsius in nitrogen ambient for about five minutes. Next, a backside contact mask is placed over the photoresist and exposed under ultra violet light for about ten seconds. The wafer 300 is then inserted in a developer for about one and a half minutes to develop the photoresist. The wafer 300 is rinsed in de-ionized, blow dried, and baked again for five minutes in nitrogen ambient at 90 degrees Celsius.

Nickel may be electroplated on the portion of the nickel seed layer not protected by the photoresist. The dissolution of the photoresist may be accomplished with acetone and subsequent rinsing in de-ionized water. Using the thick nickel as an etch mask, the backside of the wafer 300 is etched to expose the layer 302, which is the first bondpad layer. The thickness of the electroplated nickel should be such that it is completely etched just before the bondpads are exposed. This permits a complete removal of the nickel and the etching continues on the entire backside of the wafer 300 until the bondpads are exposed. The wafer 300 is un-mounted from the carrier by immersing in acetone.

During re-entry of the space vehicle into Earth, the thermal protection system 200 may encounter thermophysical effects (shock, radiation, ionization, non-equilibrium chemistry) that combine to lead to its ablation and subsequent recession. As the thermal protection system 200 recedes, the sensors 10, 15a, 15b, 80, 85, 90 also recede. This results in a change in an electrical property of the sensors 10, 15a, 15b, 80, 85, 90 such as a change in the capacitance or resistance of the sensors 10, 15a, 15b, 80, 85, 90. For example, if the sensor 10, 85, 90 is arranged in a ladder network, then the rate of breaks of the steps of the ladder network (or the rate at which one of the electrical components separates from the other electrical components) directly relates to the recession rate of the thermal protection system 200. In cases where the recession across the thermal protection system 200 is asymmetric, such effect would be reflected on the sensor 10, 15a, 15b, 80, 85, 90 that corresponds to that location.

In an embodiment, the system and method disclosed herein may be utilized to enhance temperature and recession measurements and/or may significantly aid in optimizing the geometric shape of the susceptible material 42, such as an aero-shell of a space vehicle. Instead of having a few measurement plugs as in prior art devices, hence few measurement locations, the present disclosure provides a system and method permitting temperature and ablation recession sensors 10, 15a, 15b, 80, 85, 90 to be arrayed over a larger surface area, such as a larger surface area of the thermal protection system material 200. Each sensor 10, 85, 90 may comprise one or more resistors, such as a micro-millimeter scale resistor ladder network, fabricated in materials that are compatible with the susceptible material. The resistor ladder network may be fabricated in the substrate 12 and released. Each resistor ladder network is positioned along the thickness of the susceptible material 42. The sensors 15a, 15b, 80 which may be capacitor strips, may be positioned adjacent each of the sensors 10 to determine a change in the thickness of the susceptible material (recession rate).

The invention claimed is:

1. A system comprising:
    a material susceptible to corrosion or ablation and having a thickness defined between a first end and a second end;
    a first sensor and a second sensor on the material and extending along the thickness adjacent the first end and toward the second end, the first sensor having an electrical component that changes an electrical property of the sensor as temperature of the material changes, and wherein the second sensor has an electrical property that is constant with respect to changes in temperature of the material,
    an electrical circuit coupled to the first sensor and the second sensor to determine the change in the electrical property of each of the first sensor and the second sensor; and
    a processor determining a thickness and a temperature of the material based on the change of the electrical property of the first sensor and the second sensor; wherein the second sensor has a capacitance configured to change as a length of the second sensor changes.

2. The system of claim 1 wherein the first sensor comprises at least one resistor ladder network sensor and further wherein the second sensor comprises at least one capacitor strip sensor.

3. The system of claim 1 wherein the first sensor and the second sensor are arranged in ladder networks.

4. The system of claim 3 further comprising a third sensor having a capacitor strip for measuring the thickness of the material.

5. The system of claim 4 wherein the processor determines the thickness of the material from the electrical property of the second sensor and the third sensor, and further wherein the processor compares the thickness of the material as computed from changes in the electrical property of the second sensor with the thickness of the material as computed from changes in the electrical property of the third sensor.

6. The system of claim 1 wherein the ablation or the corrosion causes a first portion of the first sensor to electrically separate from a second portion of the first sensor.

7. The system of claim 1 wherein the change in the electrical property of the first sensor is an increased resistance and further wherein a change in the second sensor is a decreased capacitance.

8. The system of claim 1 wherein the first sensor has a plurality of resistors and further wherein at least one of the plurality of resistors having a non-zero temperature coefficient such that resistance changes with temperature.

9. The system of claim 1 wherein the processor determines the temperature of the material based on the electrical property of the first sensor and further wherein the processor determines the thickness of the material based on the second sensor.

10. The system of claim 1 further comprising a thermoelectric device configured to scavenge energy from the material and power the first sensor or the second sensor.

11. A method comprising the steps of:
positioning a first micro electric sensor and a second micro electric sensor within a susceptible material;
applying a current or voltage to the first micro electric sensor and the second micro electric sensor;
exposing the susceptible material to a substance causing a change in a temperature and thickness of the susceptible material;
determining the temperature of the susceptible material from an electrical property of the first micro electric sensor; and
determining the thickness of the susceptible material from an electrical property of the second micro electric sensor, wherein the electrical property of the first micro electric sensor changes more with temperature than the second micro electric sensor; wherein the second micro electric sensor has a capacitance configured to change as a length of the second micro electric sensor changes.

12. The method of claim 11 further comprising positioning a third micro electric sensor within the susceptible material adjacent the first micro electric sensor and the second micro electric sensor, wherein the step of determining the thickness of the susceptible material is based on analyzing the electrical property of the second micro electric sensor and the third micro electric sensor.

13. The method of claim 12 wherein the step of determining the temperature of the susceptible material comprises comparing the electrical property of the first micro electric sensor and the third micro electric sensor.

14. The method of claim 12 further comprising generating a tomographic image of a thickness of the material based on changes of the electrical property of the first sensor, the second sensor and the third sensor.

15. The method of claim 11 further comprising electrically separating or destroying a portion of the first sensor, the second sensor or the third sensor as a result of the change in the thickness of the susceptible material.

16. The method of claim 11 wherein the electrical property of the first sensor is resistance and the electrical property of the second sensor is capacitance.

17. A method comprising the steps of:
embedding a plurality of sensors within a material, the plurality of sensors comprising at least a first ladder sensor, a second ladder sensor, and a capacitor strip, the second ladder sensor having more rungs than the first ladder sensor, wherein the second ladder sensor having electrical components that are less temperature sensitive than electrical components of the first ladder sensor;
applying a current or voltage to each of the plurality of sensors;
exposing the material to a change in temperature causing a change in an electrical property of at least the second ladder sensor;
ablating a portion of the material to change an electrical property of at least the first ladder sensor and the capacitor strip;
determining a temperature of the material based on the change in the electrical property of the first ladder sensor and the second ladder sensor; and
determining a thickness of the material based on the change of the electrical property of the capacitor strip and the change of the electrical property of the second ladder sensor; wherein the second ladder sensor has a capacitance configured to change as a length of the second ladder sensor changes.

18. The method of claim 17 wherein the first ladder sensor and the second ladder sensor are micro resistance ladder sensors and a portion of the change of the electrical property of the first ladder sensor and the second ladder sensor is based on a change in resistance.

19. The method of claim 17 wherein the material is a braking material of a vehicle, a pipe conduit, or a thermal protection system of a space vehicle.

* * * * *